United States Patent [19]

Dippel et al.

[11] Patent Number: 4,933,568
[45] Date of Patent: Jun. 12, 1990

[54] DEVICE FOR TESTING WEB-LIKE PLANAR STRUCTURES MOVING AT HIGH SPEED

[75] Inventors: Dieter Dippel; Alexander Gausa, both Bielefeld, Fed. Rep. of Germany

[73] Assignee: Feldmuehle Aktiengesellschaft, Duesseldorf, Fed. Rep. of Germany

[21] Appl. No.: 391,584

[22] PCT Filed: Dec. 24, 1988

[86] PCT No.: PCT/EP88/01201
§ 371 Date: Aug. 28, 1989
§ 102(e) Date: Aug. 28, 1989

[87] PCT Pub. No.: WO89/06787
PCT Pub. Date: Jul. 27, 1989

[30] Foreign Application Priority Data

Jan. 12, 1988 [DE] Fed. Rep. of Germany ....... 3800543

[51] Int. Cl.⁵ .............................. G01N 21/88
[52] U.S. Cl. .................... 250/572; 250/563; 250/236; 356/431
[58] Field of Search ............... 350/627, 6.7, 6.8, 6.9, 350/6.91; 356/431, 430, 444; 250/562, 563, 571, 572, 235, 236

[56] References Cited

U.S. PATENT DOCUMENTS

| 3,972,583 | 8/1976 | Lobb | 350/6.8 |
| 4,013,367 | 3/1977 | Nagao et al. | 356/431 |
| 4,085,322 | 4/1978 | Sick | 250/227 |
| 4,302,105 | 11/1981 | Sick | 356/237 |

FOREIGN PATENT DOCUMENTS 0159700 10/1985 European Pat. Off. .
2169097 7/1986 European Pat. Off. .

Primary Examiner—David C. Nelms
Assistant Examiner—George C. Beck
Attorney, Agent, or Firm—Felfe & Lynch

[57] ABSTRACT

Web-like planar structures 10 are tested by means of a light source 11 which directs a light beam 4 onto a rotating mirror wheel 5. The light beam is projected onto the web 10 to be tested via a stationary folding mirror 1 which is centered above the web to be tested. The folding mirror 1 is composed of at least two mirror surfaces 2, which form an obtuse angle α to each other. The light beam 4 coming from the polygonal surface 14 of the mirror wheel 5 covers successively all mirror surfaces 2 of the folding mirror 1 during the rotation of the mirror wheel 5. The number of scannings of the web-like planar structures 10 per polygonal surface 14 is increased, corresponding to the number of mirror surfaces 2.

7 Claims, 5 Drawing Sheets

DEVICE FOR TESTING WEB-LIKE PLANAR STRUCTURES MOVING AT HIGH SPEED

BACKGROUND OF THE INVENTION

The invention relates to a device for testing web-like planar structures such as films, paper, sheet metal webs or glass webs, which move at a high speed, for surface irregularities and/or inclusions. The device has a light source, preferably a laser, from which a light beam is directed onto a rotating mirror wheel and projected onto the web to be tested via a stationary mirror configured as a folding mirror for the beam path and centered over the web to be tested. The reflected or passed light is sensed by a photoelectric transducer and supplied to an evaluation station.

Systems of this type are widely used and are known, for example, from the German patent publication Nos. 33 38 802; 83 100 964; 32 48 782; 83 101 095; 32 08 042; 31 29 808; and 24 11 407. Common to all of these systems is that the testing speed is determined by the rotational speed and the number of mirror facets of the mirror wheel which scans a light spot across the surface to be tested.

Presently, conventional mirror wheels operate in the range of 15,000 to 30,000 rpm. The mirror wheels are very likely to be destroyed if they rotate at higher speeds. Conventionally, the mirror wheels are vitreous bodies having facets with a reflective coating. Usually the mirror wheels have 10 facets but wheels with up to 20 facets have also been manufactured.

A pencil-shaped light beam, conventionally a laser beam, impinges on the mirror wheel. By rotating the mirror wheel, and consequently the facets, the beam is deflected and directed over the width of the web to be tested. If the web is very large then the mirror wheel must necessarily be disposed very high above the web, a fact which leads to a significant total height of the equipment. Therefore, it has already been suggested to dispose the mirror wheel relatively close to the web to be tested and to project the scanning beam first onto a stationary mirror disposed above the web which, in turn, directs the reflected beam onto the web. The same length of the beam and the same possible scanning width result in a shorter total height of the testing device since the mirror serves as an optical folding mirror. In particular, with same beam length the use of a single folding mirror makes it possible to reduce the total height of the equipment by one half. The use of several mirrors permits an even further reduction in the total height.

On the basis of conventional speeds of 15,000 rpm and 10 facets on the mirror wheel, there are 150,000 beam scans per minute. From the viewpoint of quietness of the motor drive, on one hand, and the strength of the mirror wheel, on the other, this scanning frequency approaches the mechanical limit of the system. At the same time, this frequency sets a limit on the speed of the web to be tested since a complete testing requires a slight overlapping of the flying light spot projected onto the web in consecutive scans. The size of the light spot cannot be increased at will since irregularities onto which the flying light spot impinges affect the intensity of the transmitted or reflected light in a percentage corresponding to the spot area obscured by the irregularity. Minor irregularities result in too small a contrast, and consequently do not permit an exact evaluation, by larger light spots.

SUMMARY OF THE INVENTION

A principal object of the present invention is to increase the scanning frequency without increasing either the mirror wheel speed above that which is considered to be reliable or the number of facets on the mirror wheel and, consequently, the diameter of the mirror wheel.

This object, as well as other objects which will become apparent from the discussion that follows, is achieved, according to the present invention, by providing a folding mirror of at least two mirror surfaces related to each other in an obtuse angle, the dividing line between these surfaces running parallel to the moving direction of the web to be tested, and providing a beam splitter interposed in the light beam between mirror wheel and folding mirror.

By subdividing the folding mirror into at least 2 mirror surfaces, and by directing the light beam over both mirrors the angular arrangement of the mirrors to each other causes the scanning beam to twice cover the web to be tested. This doubles the scanning frequency. The use of additional mirror surfaces—according to the preferred embodiment up to twenty mirror surfaces—permits a further increase in the scanning frequency up to twenty times the frequency with a single folding mirror. A conventional mirror wheel with 10 facets can thus produce up to 3,000,000 scans per minute as compared to 150,000 with previously known devices of this type. At this rate of scan a scanning spot size of 1.2 mm in diameter can handle web speeds of more than 3,000 meters per minute.

According to the preferred embodiment of the invention, the size of the individual mirror surfaces is in the range of 20 to 1000 mm. This size, as well as the width of the web determine the spacing between the folding mirror and the mirror wheel; that is, a smaller mirror which is disposed at a smaller distance from the mirror wheel requires a greater total height of the device unless additional, series-connected folding mirrors are used to split up the optical light path.

The beam splitter interposed between mirror wheel and folding mirror separates an auxiliary beam from the scanning beam to activate a synchronization strip which is associated with the mirror wheel according to an advantageous embodiment of the invention. The pulses derived from the synchronization strip are supplied to a computer and reduce the aperture during the transition from mirror surface to mirror surface. This eliminates error messages caused by the transition of the scanning beam from one mirror to another since, in this transition area, the scanning beam is either not reflected at all or is multiply reflected onto the web.

According to another advantageous embodiment of the invention, the angle α between the individual mirror surfaces of the folding mirror is in the range of 130 to 176 degrees. The lower range of angles is selected if only a few, for example two, mirror surfaces are provided; the higher range—i.e., the range with the more obtuse angles—is used when a larger number of mirror surfaces are provided.

For a full understanding of the present invention, reference should now be made to the following detailed description of the preferred embodiments of the invention and to the accompanying drawings.

DETAILED DESCRIPTION OF THE PREFERRED EMBODIMENT

Figure 1:
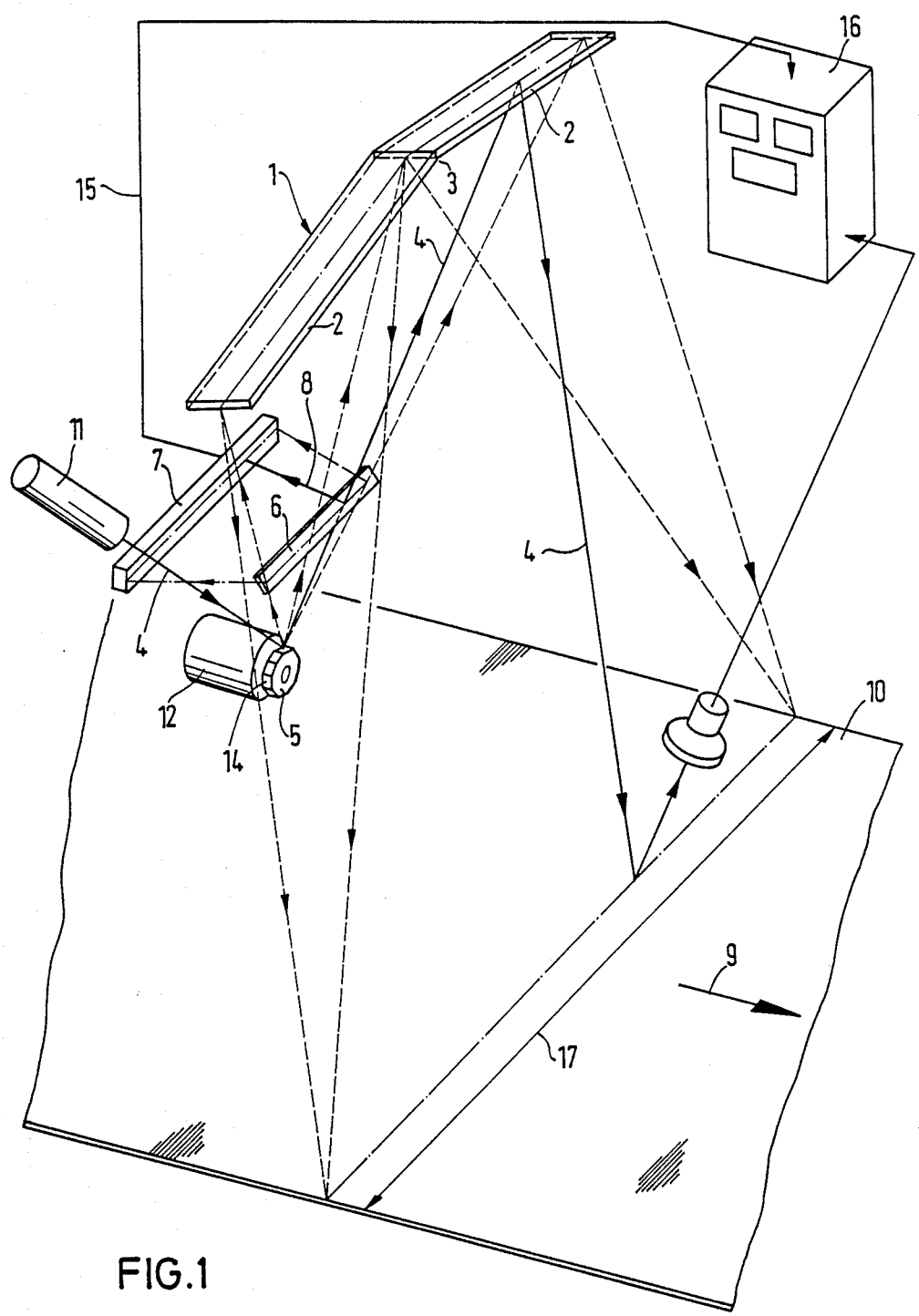
FIG. 1 is a perspective view of testing device according to the preferred embodiment of the present invention.
Figure 2:
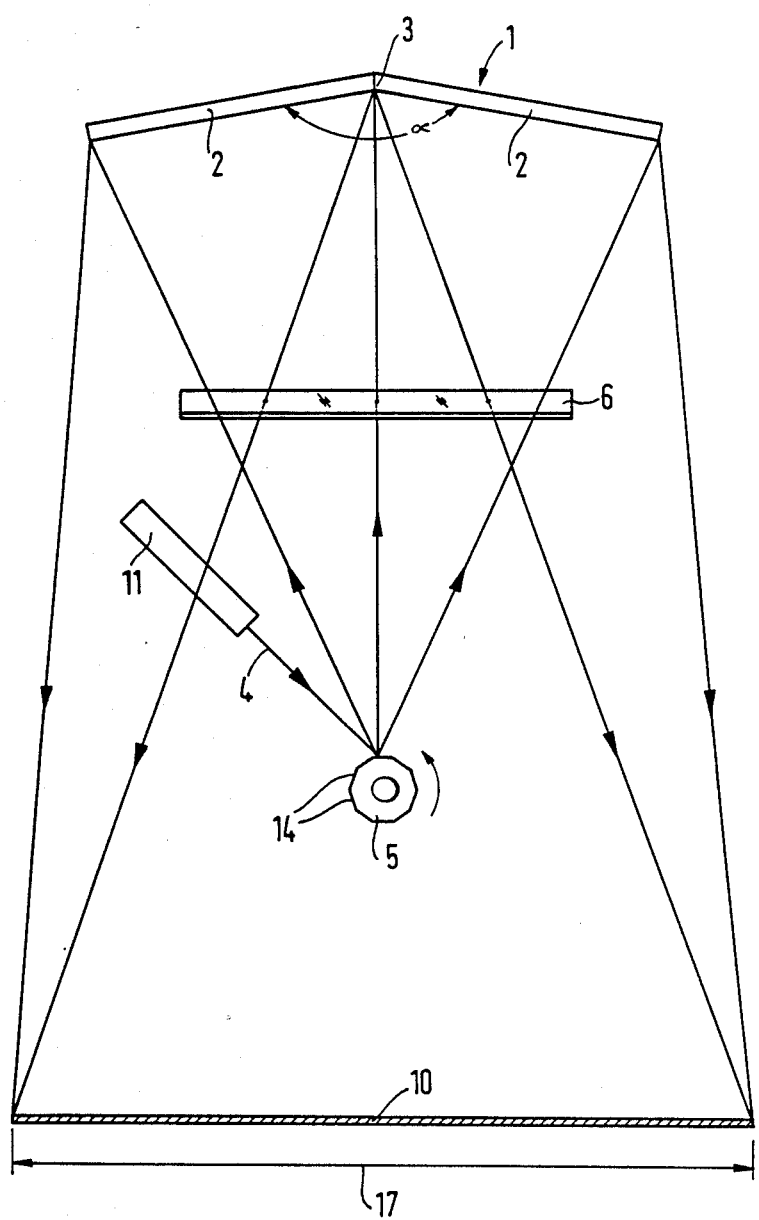
FIG. 2 and FIG. 3 are representational diagrams showing the course of a scanning beam for a folding mirror having two and twelve mirror surfaces, respectively.

As shown in FIGS. 1 and 2, 4 and 5, a laser 11 projects a light beam 4 onto a polygonal mirror wheel 5 which is driven by a motor 12. The individual polygonal surfaces 14 of the mirror wheel 5 reflect the light beam 4 in the direction of a folding mirror 1. First, the light beam 4 passes through a beam splitter 6 where an auxiliary beam 8 is separated. This auxiliary beam 8 is directed to a synchronization strip 7 which is connected to a computer 16 via a synchronization line 15. The laser 11, wheel 5 and folding mirror 1 are all contained in a protective housing 13.

After passing the beam splitter 6, the light beam 4 reaches the folding mirror 1 and impinges on one of the mirror surfaces 2 is reflected onto a web 10 to be tested, which moves in a direction shown by the arrow 9. During scanning the beam traverses the entire scanning width 17 before it reaches the second mirror surface 2 which is separated from the first mirror surface 2 by a dividing line 3.

Figure 3:
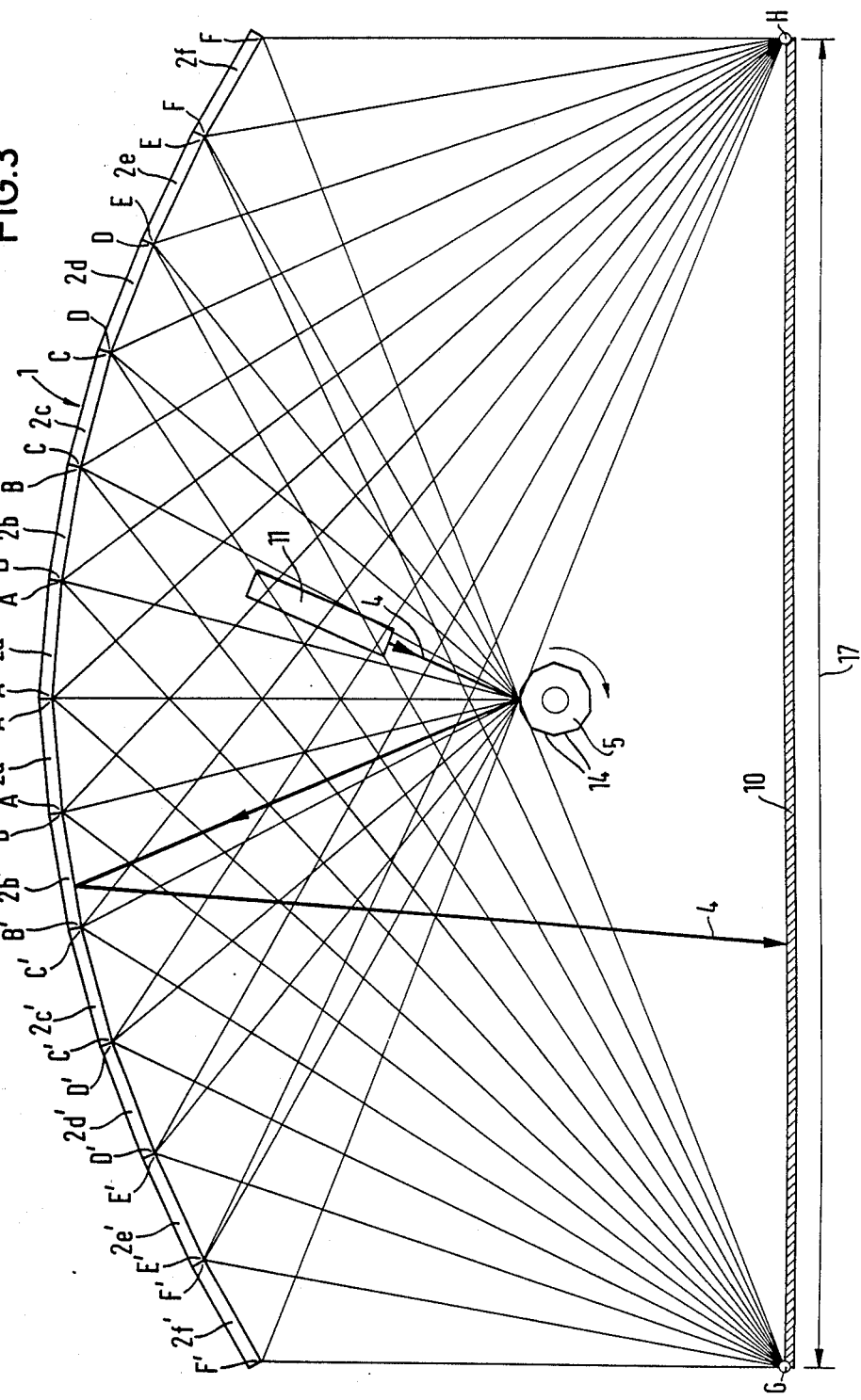
Figure 4:
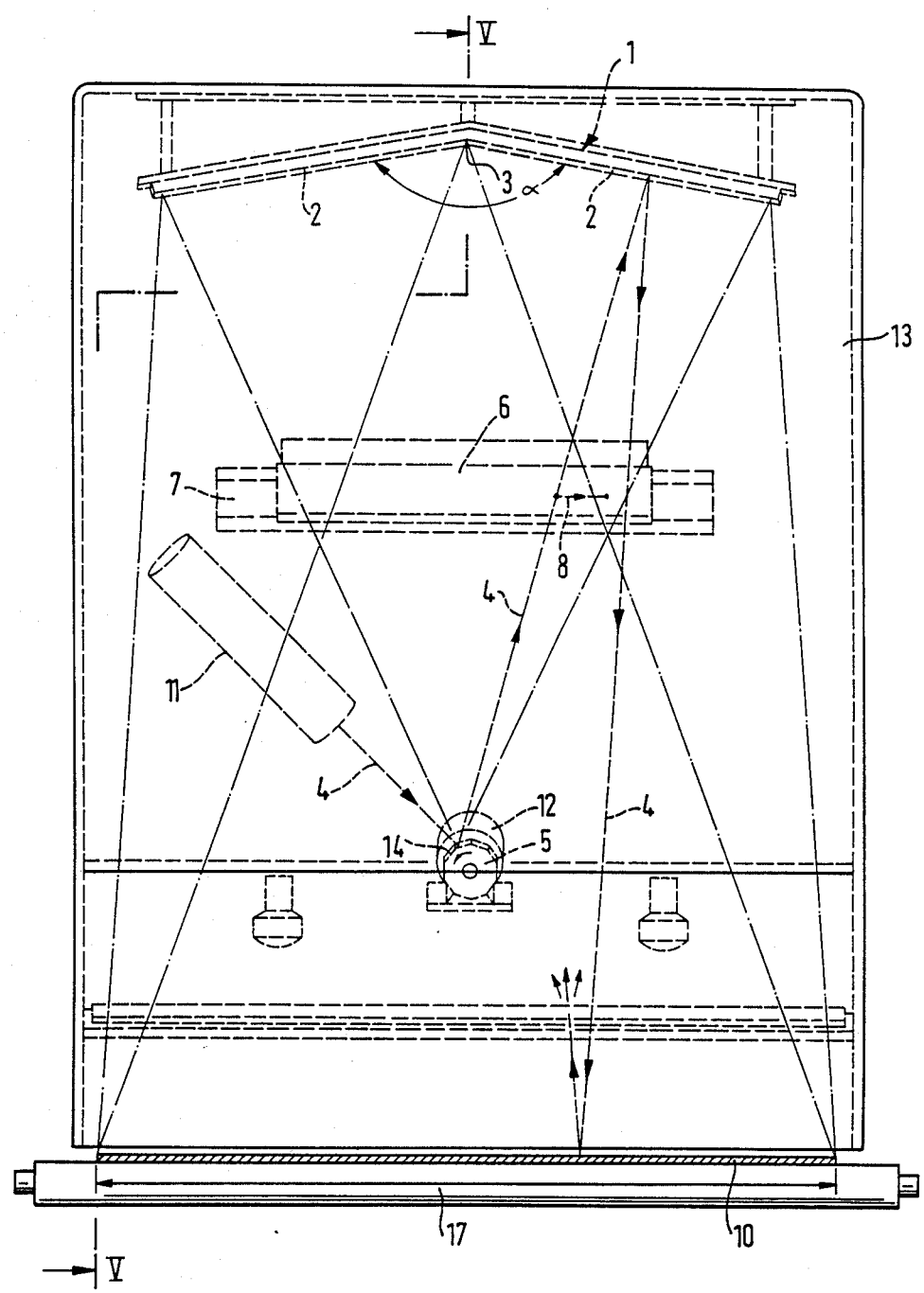
FIG. 4 is a side elevational view of the testing device of FIG. 1.
Figure 5:
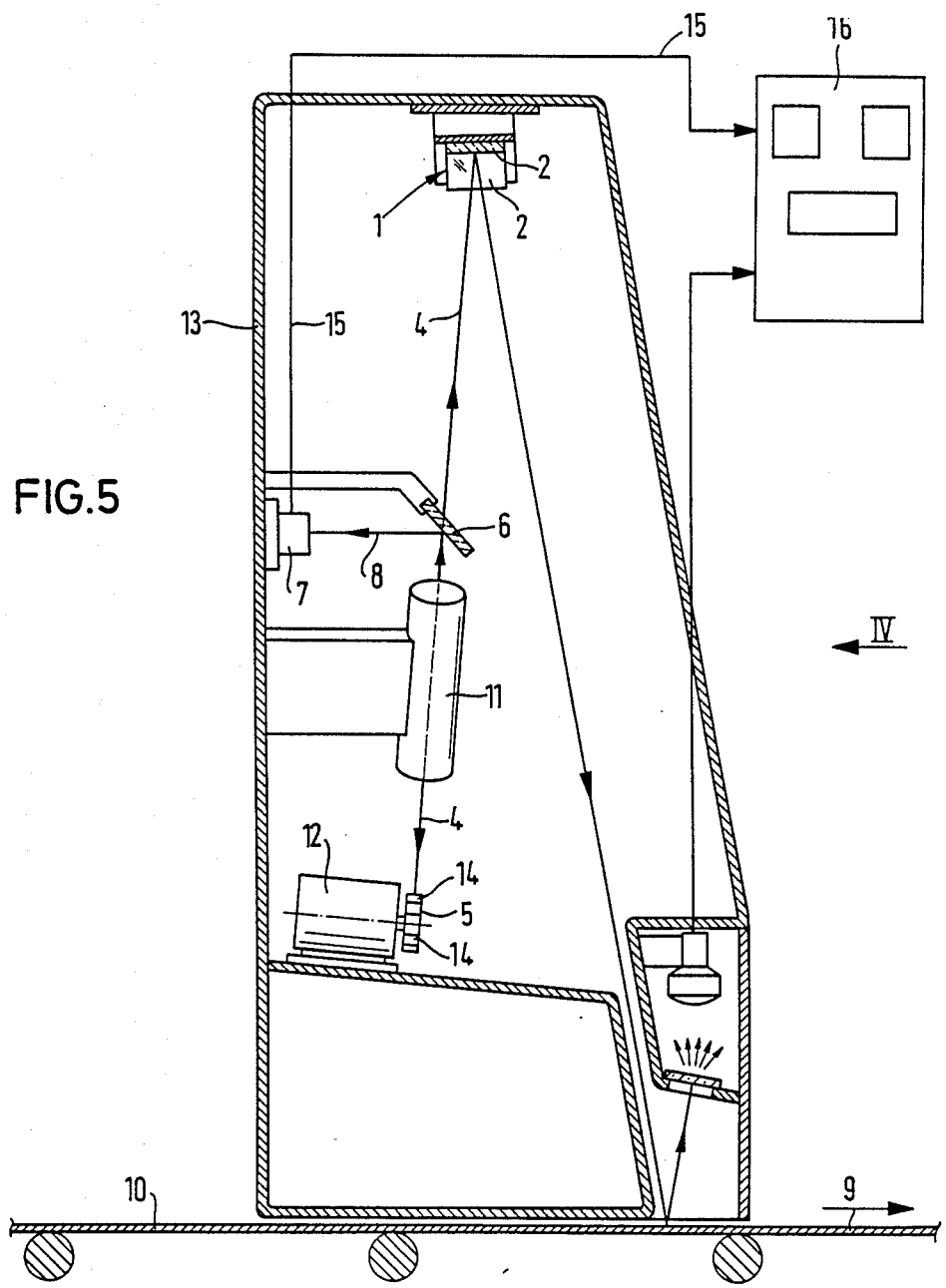
FIG. 5 a cross-sectional view taken along the line V—V in FIG. 4.

FIG. 3 represents a folding mirror 1 which is provided with twelve mirror surfaces 2; the surfaces are designated as 2a to 2f on the right side and 2a' to 2f' on the left side. The individual length of the mirror surfaces 2 is 170 mm i.e., the total length of the folding mirror 1 amounts to approximately 2 m. This design permits a scanning width 17 of approximately 2 m. The mirror wheel 5 is represented in a position where the light beam 4 emitted by the laser 11 is reflected from the polygonal surface 14 onto the mirror surface 2b'. A clockwise rotation of the mirror wheel 5 causes the light beam 4 to move over the length of the mirror 2b between points B' and B'. From here it is reflected onto the web 10, covering the entire scanning width 17 between points G and H. The simplified representation in FIG. 3 does not show the distances between the folding mirror 1 and the points G and H and the mirror wheel in their correct relationship. This diagram shows different angles of incidence and reflection which, of course, do not occur in the practice.

When the mirror wheel 5 continues to turn, the light beam 4 impinges on the mirror surface 2a' which is defined by points A'—A'. In this way, a field is scanned that is defined by points A'—A', H and G; i.e., again the entire scanning width 17. A further rotation of the mirror wheel 5 admits the light beam 4 to the mirror surfaces 2a, 2b, 2c, 2d, 2e, and 2f. Subsequently, the light beam impinges from the laser 11 onto the next polygonal surface 14 of the mirror wheel 5 and deflects the light beam 4 onto the mirror surface 2f' thus covering the area between points F'—F'. From each polygonal surface 4 the light impinges analogously on each mirror surface 2f and each mirror surface 2 reflects the light beam 4 such that it covers the scanning width 17 between points G and H.

There has thus been shown and described a novel testing device which fulfills all the objects and advantages sought therefore. Many changes, modifications, variations and other uses and applications of the subject invention will, however, become apparent to those skilled in the art after considering this specification and the accompanying drawings. All such changes, modifications, variations and other uses and applications which do not depart from the spirit and scope of the invention are deemed to be covered by the invention which is limited only by the claims which follow.

What is claimed is:

1. In a device for testing web-like planar structures moving at a high speed for surface irregularities and/or inclusions, said device comprising a light source for producing a light beam; a rotating mirror wheel that projects the light beam onto a stationary mirror; said stationary mirror, which is configured as a folding mirror to redirect the beam onto the web to be tested, being centered above the web to be tested; and photoelectric transducers for sensing the reflected light and/or the light passed through the web and for supplying a signal to an evaluation station; the improvement wherein the folding mirror is composed of at least two mirror surfaces which form an obtuse angle $\alpha$ with respect to each other, the dividing line of which extends parallel to the moving direction of the web to be tested, and wherein a beam splitter is incorporated in the light beam path between mirror wheel and the folding mirror.

2. The device in accordance with claim 1, wherein the folding mirror has two to twenty mirror surfaces.

3. The device in accordance with claim 1, wherein each mirror surface has a length in the range of 20 to 1,000 mm.

4. The device in accordance with claim 1, wherein the angle $\alpha$ between the individual mirror surfaces is in the range of 130 to 176 degrees.

5. The device in accordance with claim 1, wherein the mirror wheel is optically associated with a synchronization strip.

6. The device in accordance with claim 1, wherein an auxiliary beam separated from the light beam impinges onto a synchronization strip.

7. The device in accordance with claim 1, wherein apertures of the transitions from one mirror surface to another mirror surface are reduced by pulses supplied from a synchronization strip.

* * * * *